United States Patent [19]

Alexander

[11] 4,356,709

[45] Nov. 2, 1982

[54] ICE CAP

[76] Inventor: Dixie F. Alexander, 6390 Center Dr., Redding, Calif. 96001

[21] Appl. No.: 239,390

[22] Filed: Mar. 2, 1981

[51] Int. Cl.³ .......................... F25D 3/08; F25D 23/12
[52] U.S. Cl. ..................................... 62/530; 62/259.3; 128/402; 150/2.3
[58] Field of Search ...................... 128/402, 399, 254; 150/2.3; 62/259.3, 530

[56] References Cited

U.S. PATENT DOCUMENTS

| 1,964,655 | 6/1934 | Williamson | 150/2.3 |
| 2,158,571 | 5/1939 | Culp | 150/2.3 |
| 3,090,045 | 5/1963 | Hurst | 150/2.3 X |
| 3,349,825 | 10/1967 | Andreadis | 150/2.3 |
| 4,133,055 | 1/1979 | Zebuhr | 150/2.3 |
| 4,204,543 | 5/1980 | Henderson | 128/402 |

Primary Examiner—Lloyd L. King
Attorney, Agent, or Firm—Blair, Brown & Kreten

[57] ABSTRACT

An ice cap for a wearer's head which includes a bag having inner and outer walls lined interiorly with plastic which define a cavity to be filled with ice through an opening in the bag arranged to be sealed with a removable VELCRO panel, the bag having a marginal edge defining an opening for positioning of the bag on the scalp of the wearer's head with an elastic band extending throughout the marginal edge for yieldably retaining the bag on the wearer's head.

1 Claim, 2 Drawing Figures

ICE CAP

BACKGROUND OF THE INVENTION

It has long been known to apply cold compresses to a wearer's head for the alleviation of pain. One well known technique involves the utilization of a washcloth or the like which is soaked in cold water and applied to the head, the cold water with which the cloth is soaked being repeatedly replenished to maintain the desired low temperature. The limitations of such a technique are well known being not only an awkard procedure but frequently resulting in water pouring down the head of the wearer and onto the wearer's apparel. Another technique involves the use of an ice bag filled with ice which is merely placed on top of the head thereby providing a localized source of cold temperature.

It has been found that in the treatment of patients with a technique know as chemotherapy one of the side effects of such a treatment is the loss of hair on the part of the patient. While many techniques have been proposed to prevent such loss of hair, since techniques have been generally unsuccessful. However, it has been discovered that the application of a low temperature to the scalp area of a patient undergoing chemotherapy has been beneficial in eliminating or substantially reducing such hair loss. Unfortunately, the prior art does not provide any suitable device for the application of cold to the entire scalp area.

The following U.S. Pat. Nos. are representative of the prior art to which the subject invention pertains all of which are clearly distinguishable both structurally and functionally from applicant's invention:

1,964,655 Williamson
3,696,814 Umemoto
3,780,537 Spencer
3,840,918 Shave
4,172,495 Zebuhr et al.

The Williamson patent relates to an ice bag which is somewhat in a nature of a belt, but which may be filled with ice and buckled around a selected portion of a wearer's face or head. The Umemoto patent relates to a headgear for supplying water to evaporatively cool and forehead and upper portion of a wearer's head. The Shave patent relates to a therapeutic pillow and the Spencer patent to an envelope of plastic material containing a gel for use as a hot and cold compress. The Zebuhr et al. patent relates to a slurry-cooled helmet wherein a plurality of tubes connected to a source of cooled slurry are utilized to circulate the cooled slurry through a headgear for athletic activities.

OBJECTS AND SUMMARY OF THE INVENTION

Accordingly, a primary object of this invention is to provide a new and novel ice cap for the application of cold to the scalp of a wearer's head.

Another object of this invention is to provide a new and novel ice cap which prevents the loss of hair during chemotherapy treatment and the like.

A further object of this invention is to provide a new and novel ice cap which covers the scalp area of a wearer's head, which may be easily filled with ice and which is capable of prolonged use without deterioration.

Still another object of this invention is to provide a new and novel ice cap which is simple and inexpensive in construction and which is positively retained on the head of the user during use for therapeutic purposes.

The objects of the invention and other related objects are accomplished by the provision of a bag having a substantially circular, marginal edge portion defining an opening for receiving the upper portion of a wearer's head with the bag in overlying relationship with the scalp of the wearer. The bag includes an outer wall and an inner wall defining a sealed cavity to be filled with ice, with the bag outer wall having a fill opening with a detachable closure of the Velcro type. An elastic band is connected to the bag which extends throughout the bag marginal edge portion for retaining the bag in the worn position on the wearer's head.

Other objects and advantages will become apparent in the following specification when considered in light of the attached drawings.

DESCRIPTION OF THE PREFERRED EMBODIMENT

Figure 1:
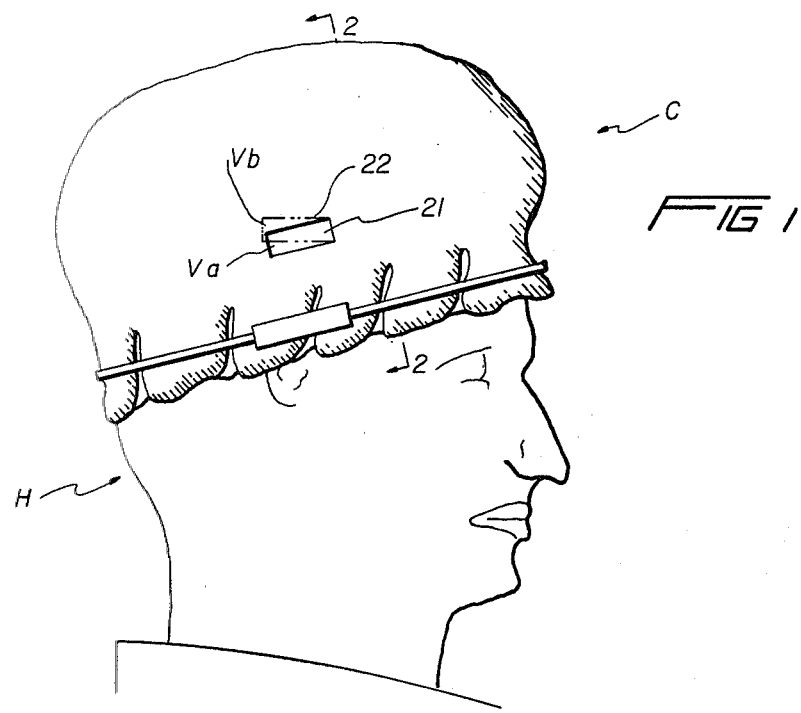
FIG. 1 is a side view of a wearer's head showing the bag in the worn position.

Referring now to the drawing, there is shown an ice cap constructed in accordance with the invention and designated generally by the letter C. FIG. 1 shows the cap C in an operative position on the head H of the wearer, wherein the scalp area of the wearer's head H is completely covered by the cap C.

Figure 2:
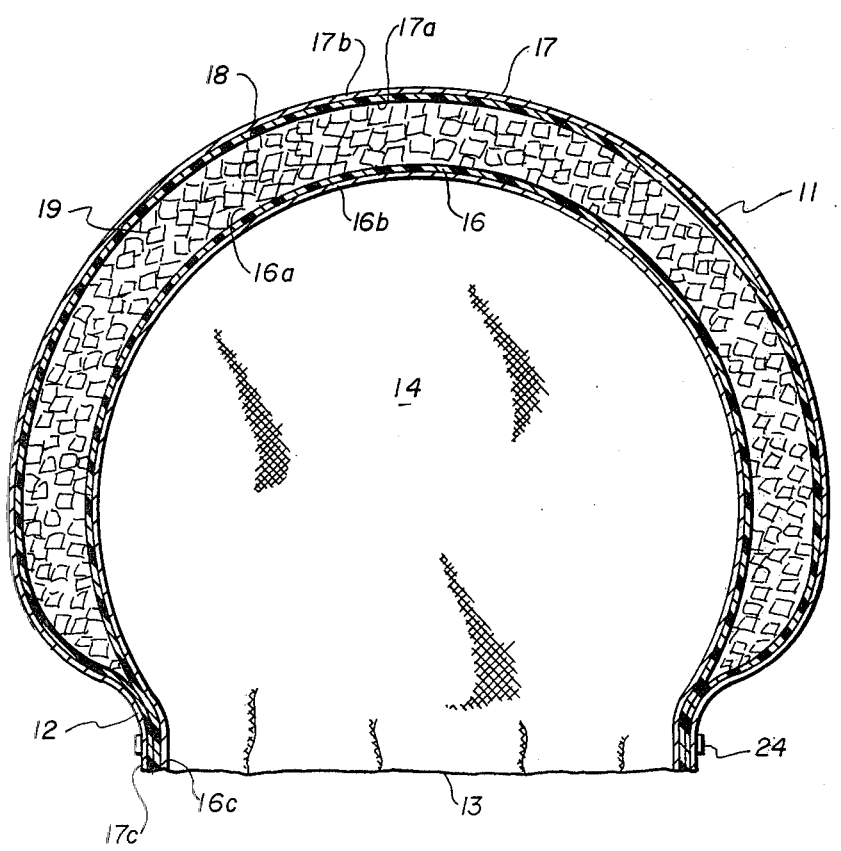
FIG. 2 is a sectional view taken substantially along line 2—2 of FIG. 1 in the directions of the arrows.

Referring now to FIG. 2, the cap C includes a bag 11 having substantially circular, marginal edge portion 12 defining an opening 13 for receiving the upper portion of the wearer's head H with the bag 11 in overlying relationship with the wearer's scalp. As can be understood, insertion of the wearer's head through the opening 13 permits the upper portion of wearer's head to be accommodated within the interior 14 of the bag.

The bag 11 includes an inner wall 16 and an outer wall 17 defining a sealed cavity 18 which is filled with ice 19. In the preferred embodiment, both the inner wall 16 and outer wall 17 are of laminated construction with inner wall 16 comprising an inner laminate 16a of moisture impervious material such as plastic or the like and an outer laminate 16b of textile material such as cloth. Similarly, the outer wall 17 includes an inner laminate 17a of moisture impervious material such as plastic or the like and an outer laminate 17b of textile material such as cloth.

In order to fill the cavity 18 with ice 19 an opening 21 is provided in the bag outer wall 17 communicating with the cavity 18 though which ice such as crushed ice may be inserted. A removable closure such as a panel 22 is provided for closing the opening 21 and, in the preferred embodiment, a Velcro device having well known component parts Va, Vb on the marginal edge of the outer surface of the outer wall 17 adjacent the opening 21 and on the inner surface of the panel 22 respectively so that the closure panel 22 may be detachably removed.

As will be noted, the inner and outer walls 16, 17 are provided with marginal edge portions 16c, 17c which are connected together in overlying relationship. In order to retain the cap C in the worn position on the head H of the wearer as shown in FIG. 1, an elastic band 24 is secured to the overlying marginal edges 16c, 17c of the inner and outer walls 16, 17 respectively in overlying relationship therewith by means of stitching or the like so that the marginal edge portion 12 of the bag 11 is yieldably retained against the wearer's head in the worn position of the cap C as shown best in FIG. 1.

Thus, in the use of the cap C for therapeutic purposes, it has been found that beneficial results are obtained when the cap cavity 18 is filled with ice and placed on the head H of the wearer approximately 45 minutes before a chemotherapy treatment. The resulting application of cold causes the hair follicles to be compressed and locked in thereby remaining in place to prevent the loss of hair.

Having thus described the preferred embodiment of the invention it should be understood that numerous structural modifications and adaptations may be resorted to without departing from the spirit of the invention.

What is claimed is:

1. An ice cap for therapeutic treatment of a wearer's scalp comprising, in combination, a bag having a substantially circular, marginal edge portion defining an opening for receiving the upper portion of a wearer's head with said bag in complete overlying relationship with the entire scalp of the wearer, said bag including an outer wall and an inner wall defining a sealed cavity to be filled with ice, said inner wall and said outer wall each include an inner and outer laminate, the inner laminates of said inner and outer walls being formed of moisture-impervious plastic material and the outer laminates of said inner and outer walls being formed of textile cloth material, said bag outer wall having an opening for filling said cavity with ice and a detachable closure for closing said opening and an elastic band connected to said bag extending throughout said bag marginal edge portion for retaining said bag in the worn position on the wearer's head, wherein said closure and the outer surface of said outer wall adjacent said opening are provided with a Velcro device for detachably mounting said closure in closing relationship with said opening, wherein the marginal edges of said inner and outer walls and said elastic band are secured together by stitching in overlying relationship.

* * * * *